United States Patent
Root et al.

(10) Patent No.: US 11,441,949 B2
(45) Date of Patent: Sep. 13, 2022

(54) METHOD AND APPARATUS FOR IDENTIFYING A RAMAN SPECTRUM FROM BACKGROUND FLUORESCENCE

(71) Applicant: CytoVeris Inc., Farmington, CT (US)

(72) Inventors: Gary Root, Cheshire, CT (US); David Fournier, Northborough, MA (US); Rishikesh Pandey, Unionville, CT (US)

(73) Assignee: CytoVeris Inc., Farmington, CT (US)

( * ) Notice: Subject to any disclaimer, the term of this patent is extended or adjusted under 35 U.S.C. 154(b) by 0 days.

(21) Appl. No.: 17/222,858

(22) Filed: Apr. 5, 2021

(65) Prior Publication Data

US 2021/0310868 A1 Oct. 7, 2021

Related U.S. Application Data

(60) Provisional application No. 63/004,995, filed on Apr. 3, 2020.

(51) Int. Cl.
*G01N 15/02* (2006.01)
*G01J 3/44* (2006.01)
(Continued)

(52) U.S. Cl.
CPC .......... *G01J 3/4412* (2013.01); *A61B 5/0075* (2013.01); *G01J 3/4406* (2013.01); *G01J 2003/4418* (2013.01); *G06N 3/04* (2013.01)

(58) Field of Classification Search
CPC ............... G01J 3/4412; G01J 3/4406; G01J 2003/4418; G01J 2003/4424; G01J 3/44;
(Continued)

(56) References Cited

U.S. PATENT DOCUMENTS

2008/0192246 A1* 8/2008 Neiss .................. G01J 3/02
356/73
2009/0097020 A1* 4/2009 Treado ................ G01N 21/65
356/301

FOREIGN PATENT DOCUMENTS

WO 2020160462 A1 8/2020

OTHER PUBLICATIONS

Beier et al. "Method for Automated Background Subtraction from Raman Spectra Containing Known Contaminants", Analyst, 134, 2009, pp. 1198-1202.
(Continued)

*Primary Examiner* — Md M Rahman
(74) *Attorney, Agent, or Firm* — Getz Balich LLC (57) ABSTRACT

A method and system for identifying a Raman spectrum component of an observed spectrum is provided. The observed spectrum is produced by interrogating a material such as a tissue sample with light at the one or more predetermined wavelengths, and the observed spectrum includes a background fluorescence component representative of fluorescent emissions resulting from the light interrogation and a Raman spectrum component representative of a Raman scattering resulting from the light interrogation. The method includes a) creating a reconstructed fluorescence spectrum representative of the background fluorescence component of the observed spectrum using one or more empirically determined fluorescent spectral profiles; and b) identifying the Raman spectrum of the observed spectrum using the reconstructed fluorescence spectrum.

25 Claims, 4 Drawing Sheets

(51) Int. Cl.
*A61B 5/00* (2006.01)
*G06N 3/04* (2006.01)

(58) Field of Classification Search
CPC ...... A61B 5/0075; A61B 5/4312; G06N 3/04; G06N 20/00; G01N 21/6486; G01N 21/65
USPC .......................................................... 356/336
See application file for complete search history.

(56) References Cited

OTHER PUBLICATIONS

Cadusch et al. "Improved Method for Fluorescence Background Subtraction from Raman Spectra", J. Raman Spectrosc. 2013, 44, pp. 1587-1595.

Chen et al. "Improved Savitsky-Golay-Method-Based Fluorescence Subtraction Algorithm for Rapid Recovery of Raman Spectra", Applied Optics, vol. 53, No. 24, Aug. 20, 2014, pp. 5559-5569.

Gebrekidan et al. "A Shifted-Excitation Raman Difference Spectroscopy (SERDS) Evaluation Strategy for the Efficient Isolation of Raman Spectra from Extreme Fluorescence Interference", Journal of Raman Spectroscopy, 47, 2016, pp. 198-209.

Guo et al. "Optimization of Raman-Spectrum Baseline Correction in Biological Application", Analyst, vol. 141, 2016, pp. 2396-2404.

Li et al. "Morphological Weighted Penalized Least Square for Background Correction", Analyst, May 20, 2013, pp. 4483-4492.

Lieber et al. "Automated Method for Subtraction of Fluorescence from Biological Raman Spectra", Applied Spectroscopy, vol. 57, No. 11, 2003, pp. 1363-1367.

Matousek et al. "Florescence Suppression in Resonance Raman Spectroscopy Using a High-Performance Picosecond Kerr Gate", Journal of Raman Spectroscopy, 32, 2001, pp. 983-988.

Zhao et al. "Automated Autofluorescence Background Subtraction Algorithm for Biomedical Raman Spectroscopy", Applied Spectroscopy, vol. 61, No. 11, 2007, pp. 1225-1232.

Vishal M. Patel et al., "Dictionary-Based Methods for Object Recognition", Handbook of Statistics, vol. 13, 2013, pp. 203-225.

* cited by examiner

METHOD AND APPARATUS FOR IDENTIFYING A RAMAN SPECTRUM FROM BACKGROUND FLUORESCENCE

This application claims priority to U.S. Patent Appln. No. 63/004,995 filed Apr. 3, 2020, which is hereby incorporated by reference in its entirety.

BACKGROUND OF THE INVENTION

1. Technical Field

The present disclosure relates to systems and methods for examining materials using Raman spectroscopy, and more specifically such systems and methods that include fluorescence background separation.

2. Background Information

Raman spectroscopy is established as an effective noninvasive tool that can be used to examine human tissue samples for a variety of different purposes. Raman spectroscopy can also be used to as a noninvasive tool for examining materials (e.g., pharmaceutical products, chemical products, food products, etc.). The ability of Raman spectroscopy to detect subtle biological differences in tissue make it a useful tool in distinguishing cancerous tissue from healthy tissue particularly in breast biopsies. A major challenge of Raman spectroscopy is the presence of autofluorescence background signals which are very often a few orders of magnitude stronger than those signals arising from Raman scattering. To effectively analyze the desired Raman signals it is necessary to account for the autofluorescence background typically by removing it or otherwise separating it. A number of different approaches have been proposed for removing background autofluorescence, including instrumental approaches (e.g., excitation wavelength shifting [1], time-gating [2], photobleaching, and the like) and computational approaches (e.g., polynomial fitting ("Poly fit") and modified multi-polynomial fitting ("ModPoly") [3-5], polynomial and contaminant fit [6], least squares approaches [7], frequency domain filtering, wavelet transformation, iterative approaches like the Savitzky Golay method [8], peak clipping [9], and the like.

All of these approaches have benefits and shortcomings. What is needed is a method and/or an apparatus for removing background autofluorescence from Raman scattering signals that is an improvement over the presently available techniques.

SUMMARY

According to an aspect of the present disclosure, a method for identifying a Raman spectrum component of an observed spectrum is provided. The observed spectrum is produced by interrogating a tissue sample with light at the one or more predetermined wavelengths, and the observed spectrum includes a background fluorescence component representative of fluorescent emissions resulting from the light interrogation and a Raman spectrum component representative of a Raman scattering resulting from the light interrogation. The method includes a) creating a reconstructed fluorescence spectrum representative of the background fluorescence component of the observed spectrum using one or more empirically determined fluorescent spectral profiles; and b) identifying the Raman spectrum of the observed spectrum using the reconstructed fluorescence spectrum.

In any of the aspects or embodiments described above and herein, the empirically determined fluorescent spectral profiles may include at least one fluorescent spectral profile of a fluorophore present within the tissue sample.

In any of the aspects or embodiments described above and herein, the fluorophore may be at least one of tryptophan, collagen, elastin, beta-carotene, nicotinamide adenine dinucleotide (NADH), flavin adenine dinucleotide (FAD), or hemoglobin.

In any of the aspects or embodiments described above and herein, the step of creating a reconstructed fluorescence spectrum may include creating a best fit between the reconstructed fluorescence spectrum and the background fluorescence component of the observed spectrum.

In any of the aspects or embodiments described above and herein, the step of creating the best fit may include weighting respective contributions of a plurality of the fluorophore spectral profiles.

In any of the aspects or embodiments described above and herein, the step of creating a reconstructed fluorescence spectrum may utilize an absorption spectral profile of a material that absorbs at least some of the background fluorescence component resulting from the light interrogation.

In any of the aspects or embodiments described above and herein, the step of creating a reconstructed fluorescence spectrum may include using a machine learning technique, and that machine learning technique may include sparse coding.

In any of the aspects or embodiments described above and herein, the step of identifying the Raman spectrum component of the observed spectrum using the reconstructed fluorescence spectrum may include subtracting the reconstructed fluorescence spectrum from the observed spectrum.

According to another aspect of the present disclosure, a method for identifying a Raman spectrum from subject tissue using Raman spectroscopy is provided. The method includes a) interrogating the subject tissue with light at the one or more predetermined wavelengths produced by at least one light source; b) determining an observed spectrum by sensing the subject tissue for light emitted from the subject tissue using one or more light detectors, the observed spectrum resulting from the light interrogation of the subject tissue, and the observed spectrum including a background fluorescence component and a Raman spectrum component; c) creating a reconstructed fluorescence spectrum representative of the background fluorescence component of the observed spectrum using one or more empirical fluorescent spectral profiles; and d) identifying the Raman spectrum component of the observed spectrum using the reconstructed fluorescence spectrum.

According to another aspect of the present disclosure, a system for identifying a Raman spectrum emitted from subject tissue is provided. The system includes at least one light source, at least one light detector, and an analyzer. The analyzer is in communication with the at least one light source, the at least one light detector, and a non-transitory memory storing instructions. The instructions when executed cause the analyzer to a) control the light source to interrogate a tissue sample with light at one or more predetermined wavelengths; b) control the light detector to sense an observed spectrum of light emitted from the subject tissue resulting from the light interrogation of the subject tissue, and to produce signals representative of the observed spectrum, the observed spectrum having a background fluorescence component representative of fluorescent emissions resulting from the light interrogation and a Raman spectrum component representative of a Raman scattering resulting from the light interrogation; c) create a reconstructed fluorescence spectrum representative of the background fluorescence component of the observed spectrum using one or more empirically determined fluorescent spectral profiles; and d) identify the Raman spectrum component of the observed spectrum using the reconstructed fluorescence spectrum.

In any of the aspects or embodiments described above and herein, wherein the instructions further cause the analyzer to weight respective contributions of each of a plurality of fluorophore spectral profiles to create a best fit between the reconstructed fluorescence spectrum and the background fluorescence component of the observed spectrum.

In any of the aspects or embodiments described above and herein, the instructions that cause the analyzer to create the reconstructed fluorescence spectrum may utilize an absorption spectral profile of a material that absorbs at least some of the background fluorescence component resulting from the light interrogation.

In any of the aspects or embodiments described above and herein, the instructions that cause the analyzer to identify the Raman spectrum component of the observed spectrum may further cause the analyzer to subtract the reconstructed fluorescence spectrum from the observed spectrum.

According to another aspect of the present disclosure, a method for identifying a Raman spectrum emitted from a material is provided. The method includes a) interrogating a material with light at the one or more predetermined wavelengths produced by at least one light source; b) determining an observed spectrum by sensing the material for light emitted from the material using one or more light detectors, the observed spectrum resulting from the light interrogation of the material, and the observed spectrum including a background fluorescence component and a Raman spectrum component; c) creating a reconstructed fluorescence spectrum representative of the background fluorescence component of the observed spectrum using one or more empirical fluorescent spectral profiles; and d) identifying the Raman spectrum component of the observed spectrum using the reconstructed fluorescence spectrum.

In any of the aspects or embodiments described above and herein, the step of creating a reconstructed fluorescence spectrum utilizes an absorption spectral profile of a second material that absorbs at least some of the background fluorescence component resulting from the light interrogation.

In any of the aspects or embodiments described above and herein, the empirically determined fluorescent spectral profiles include at least one fluorescent spectral profile of a fluorophore present within the material.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DESCRIPTION OF THE INVENTION

Figure 1:
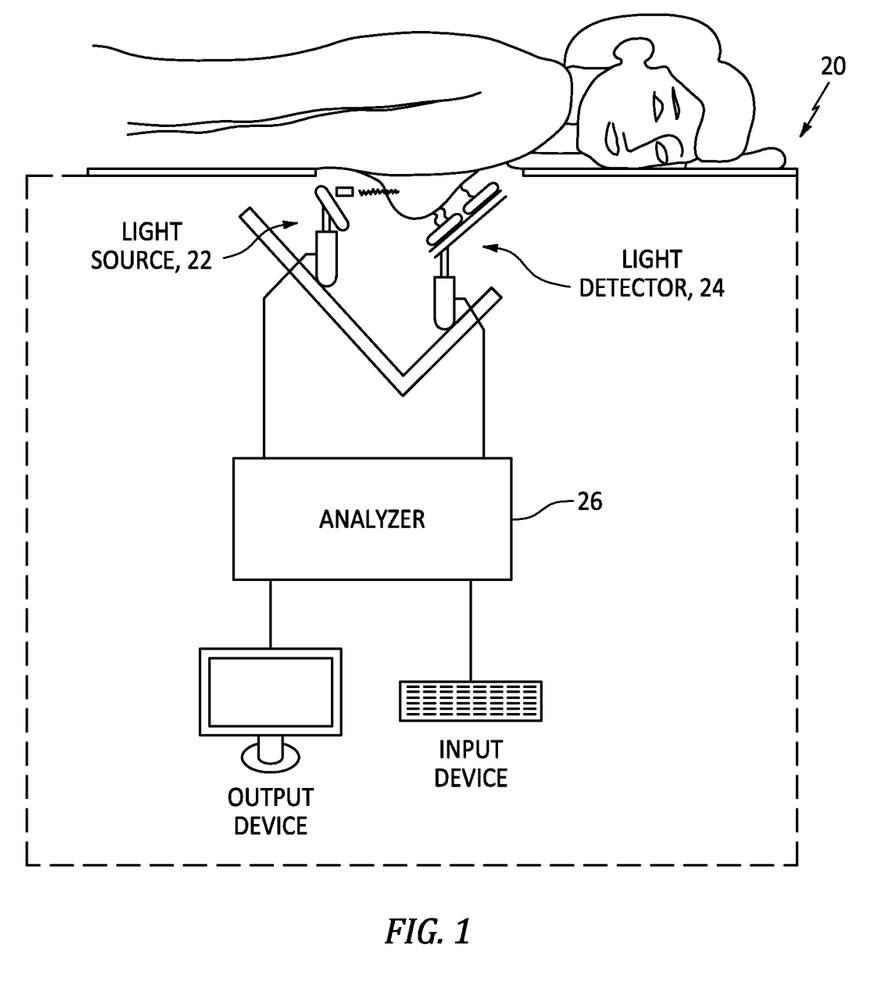
FIG. 1 is a diagrammatic illustration of a system embodiment of the present disclosure.

A diagrammatic example of a system 20 that may be used according to the present disclosure is shown in FIG. 1. The system 20 includes at least one light source 22, at least one light detector 24, and an analyzer 26. The present disclosure is not limited to this example system 20, and in alternative embodiments system 20 components may be combined or arranged in a different manner than that shown in FIG. 1 and still be within the scope of the present disclosure. The present disclosure is described below primarily in the context of a system 20 and method for examining a biological tissue sample; e.g., a breast tissue sample. As is indicated below, however, the present disclosure may be utilized with materials other than a biological tissue sample.

The light source 22 is configured to emit coherent light at wavelengths that are useful in Raman spectroscopy. An example of an acceptable coherent light source is a laser. The present disclosure is not limited to using any particular type of laser, or lasers at all. Examples of laser types include solid state, gas, diode laser or vertical-cavity surface-emitting lasers (VCSELs). The light source 22 is not limited to coherent light at any particular wavelength or wavelength band, but as indicated above coherent light at wavelengths that are useful in Raman spectroscopy are preferred. The light source 22 may be configured to produce an incident beam configured to adequately penetrate the tissue at depths where cancerous tissue may be present within the tissue body (e.g., a breast). The orientation of the incident light relative to the tissue surface may be defined by the use of a fixture, a probe, or the like. Hence, the light source 22 is operative to emit light, which light may pass through optical fibers and optics (e.g., lenses, mirror, filters, etc.), and then the emitted light may be oriented relative to the tissue surface by a fixture.

Some system 20 embodiments may include collection light optics configured to transfer, and in some instances process, light emitted from the interrogated tissue. The collection light optics may include one or more lenses, filters, dichroic mirrors, and the like for processing the received light into a desirable form.

The at least one light detector 24 is configured to receive light emitted from the interrogated tissue and produce signals representative thereof. The signals produced by the light detector 24 are transferred to the analyzer 26. Non-limiting examples of light detectors 24 include light sensors that convert light energy into an electrical signal such as a simple photodiode, or other optical detector of the type known in the art.

The analyzer 26 is in communication with other components within the system 20, such as the at least one light source 22, the at least one light detector 24, and the like to control and or receive signals therefrom to perform the functions described herein. The analyzer 26 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 20 to accomplish the same algorithmically and/or coordination of system 20 components. The analyzer 26 may include one or more memory devices and is not limited to any particular type of memory device. The analyzer 26 may include, or may be in communication with, an input device that enables a user to enter data and/or instructions, and may include, or be in communication with, an output device configured, for example to display information (e.g., a visual display or a printer), or to transfer data, etc. Communications between the analyzer 26 and other system 20 components may be via a hardwire connection or via a wireless connection.

Light interrogation of a tissue body (in-vivo or ex-vivo) at excitation wavelengths that are typically useful for Raman spectroscopic examination may be used to produce an "observed" spectrum. The term "observed" as used herein refers to the spectrum produced as a result of the light interrogation at the aforesaid excitation wavelengths during a Raman spectroscopic examination, and that may be recorded for analysis as described herein. The observed spectrum may be processed in real-time; e.g., stored in a short term memory and subsequently processed collectively at a speed so as to be considered to be done in "real-time", or may be stored/recorded for analysis at a later point in time. The observed spectrum includes a fluorescence response ("background fluorescence") as well as a Raman scattering response ("Raman spectrum). A major challenge of Raman spectroscopy is the presence of the autofluorescence background signals which are very often a few orders of magnitude stronger than those signals arising from Raman scattering. The much stronger background fluorescence can obscure the much weaker Raman spectrum. The present disclosure is configured to account for the background fluorescence component of the observed spectrum (e.g., by removing it or otherwise separating it) to facilitate analysis of the Raman spectrum. The much stronger background fluorescence component may be described as a "baseline" of the observed spectrum that can obscure the much less prevalent Raman spectrum component which has relatively small peaks and fine details. Removal of the background fluorescence component facilitates the identification and examination of the Raman spectrum component, and therefore Raman analysis of the material.

Embodiments of the present disclosure utilize an empirical database of stored fluorescent spectral profiles acquired at Raman excitation wavelength(s) that accurately represent the background fluorescence component that is convoluted with the Raman spectrum component in the observed spectrum produced during tissue interrogation. These stored fluorescent spectral profiles may be used to produce a "reconstructed fluorescence spectrum" that is representative of the background fluorescence component of the observed spectrum. In some instances, the stored fluorescent spectral profiles may be profiles of known intrinsic fluorophores found in the tissue matrix; i.e., endogenous elements present within the tissue that act as fluorophores when subjected to the interrogating light. Nonlimiting examples of intrinsic tissue fluorophores include tryptophan, collagen, elastin, beta-carotene, nicotinamide adenine dinucleotide (NADH), flavin adenine dinucleotide (FAD), hemoglobin, etc. The fluorescent spectral profiles may be collected from a variety of different sources; e.g., from testing, clinical trial data, analytical study data, etc.

Some embodiments of the present disclosure may produce a reconstructed fluorescence spectrum using an algorithmic approach; e.g., using the instructions stored within the analyzer 26. For example, the instructions may include weighting the contributions of some number of fluorescent spectral profiles to collectively produce the reconstructed fluorescence spectrum. Weighting, and other techniques may be used to minimize any difference/error between the reconstructed fluorescence spectrum and the background fluorescence component of the observed spectrum. In other words, the algorithmic approach may use the fluorescent spectral profiles and algorithmic techniques to create a "best fit" between the reconstructed fluorescence spectrum and the background fluorescence component of the observed spectrum produced from the tissue sample.

Some embodiments of the present disclosure may also be configured to account for the presence of material within the tissue sample that will absorb (i.e., attenuate) fluorescently emitted light; i.e., absorb light that is fluorescently emitted as a result of the Raman spectroscopy light interrogating the tissue sample. Non-limiting examples of a fluorescent light absorbing material that may be present in the tissue sample include tissue with a hematoma, or a tissue biopsy filler material, or the like. In such cases, the absorption spectral profile of these materials and the fluorescent spectral profiles, both within the same Raman spectral window, may be used to produce the reconstructed fluorescence spectrum. In some embodiments, the thickness of the absorbing material may also be accounted for when producing the reconstructed fluorescence spectrum as per the Beer-Lambert Law.

In some embodiments, machine learning techniques may be used to produce some or all of the reconstructed fluorescence spectrum and may be used in combination with other techniques; e.g., techniques that account for characteristics of one or more known materials known to be present within the tissue as described above. The machine learning techniques may be configured to "learn" the real features in the Raman spectrum and to avoid reproducing detrimental noise. A variety of different machine learning techniques are known, and the present disclosure is not limited to any particular machine learning technique. Sparse coding (sometimes referred to as "sparse dictionary learning") is a non-limiting example of a machine learning technique that may be used. Sparse coding is a representation learning method which aims at finding a sparse representation of the input data (e.g., components of the observed spectra) in the form of a linear combination of basic elements as well as those basic elements themselves. These elements are called "atoms" and the atoms can be collectively used to compose a "dictionary"; e.g., a collection of atoms. Sparse coding may be used to create atoms, and therefore a dictionary, from the observed spectra, or the sparse coding may use a precomputed dictionary of atoms, or any combination thereof. Sparse coding may be implemented using a "SparseCoder" object that operates as an estimator that can transform input data into a sparse linear combination of atoms. The transformation amounts to a sparse coding problem: finding a representation of the data as a linear combination of as few atoms within the dictionary as possible while maintaining a low error in the reconstructed signals. Sparsity ensures that the model is learning real features in the data and not reproducing noise. Within sparse coding, a variety of algorithms may be used, including but not limited to, "Orthogonal matching pursuit", "Least-angle regression", "Lasso", and others.

Figure 4A:
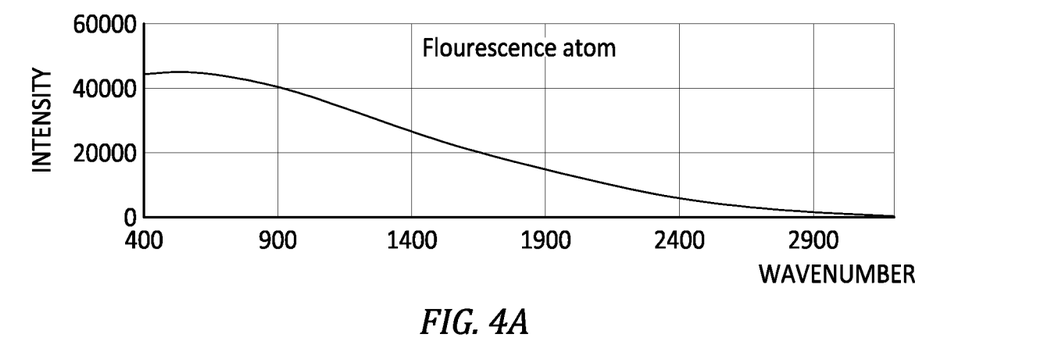
FIG. 4A is a graph of signal intensity (Y-axis) versus wavenumber (X-axis) illustrating a fluorescence atom produced using the present disclosure.
Figure 4B:
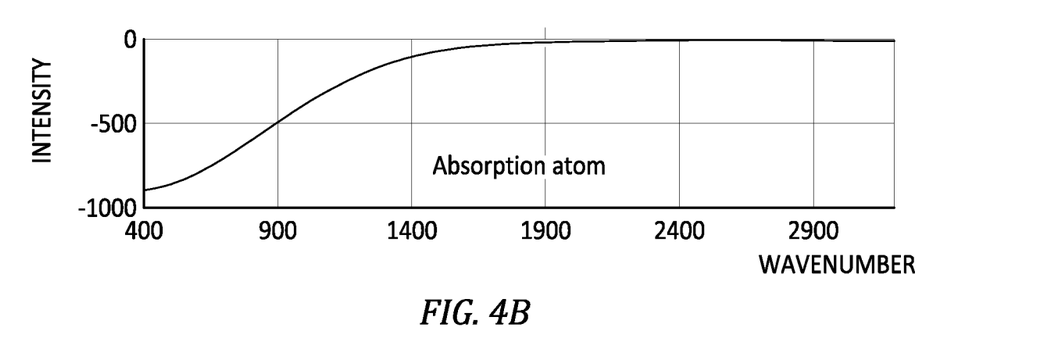
FIG. 4B is a graph of signal intensity (Y-axis) versus wavenumber (X-axis) illustrating an absorption atom produced using the present disclosure.
Figure 4C:
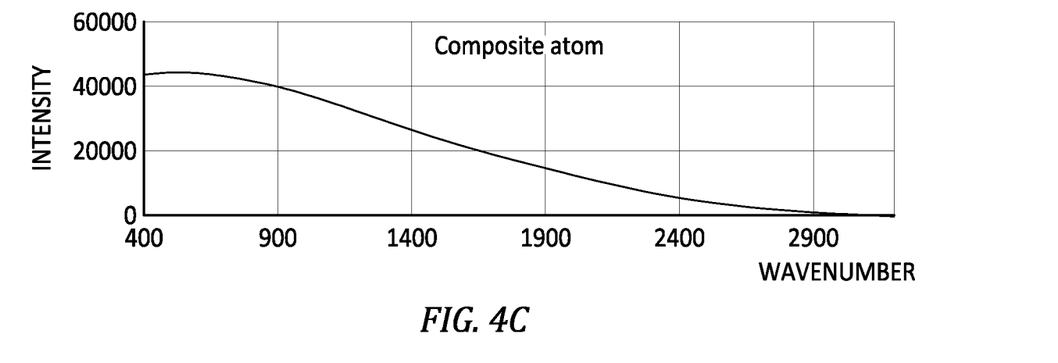
FIG. 4C is a graph of signal intensity (Y-axis) versus wavenumber (X-axis) illustrating a composite atom produced using the present disclosure.

In those embodiments of the present disclosure that utilize sparse coding and that are configured to account for the presence of material within the tissue sample that absorbs fluorescently emitted light, an "absorption" atom may also be utilized that represents a fluorescent light absorbing material (as described above) in the production of the reconstructed fluorescence spectrum. FIGS. 4A-4C discussed below illustrate how a composite atom (e.g., see FIG. 4C) may be determined using one or more atoms representative of background fluorescence produced during tissue interrogation (e.g., "fluorescence atoms"; see FIG. 4A), and one or more atoms representative of absorbed fluorescent spectrum; i.e., background fluorescence that is absorbed by material (endogenous or otherwise present) within the tissue sample (e.g., "absorption atoms"; see FIG. 4B).

The reconstructed fluorescence spectrum (regardless of how it is produced) may be subtracted from the observed spectrum (which may be recorded or analyzed in real-time) of tissue sample to remove the background fluorescence component of the observed spectrum thereby distinguishing the portion of the observed spectrum attributable to Raman scattering; i.e., the Raman spectrum component. The Raman spectrum component of the observed spectrum may then be analyzed with substantially decreased noise to ascertain the characteristics of the tissue sample; e.g., for the purpose of determining the presence or absence of cancerous tissue.

Figure 2:
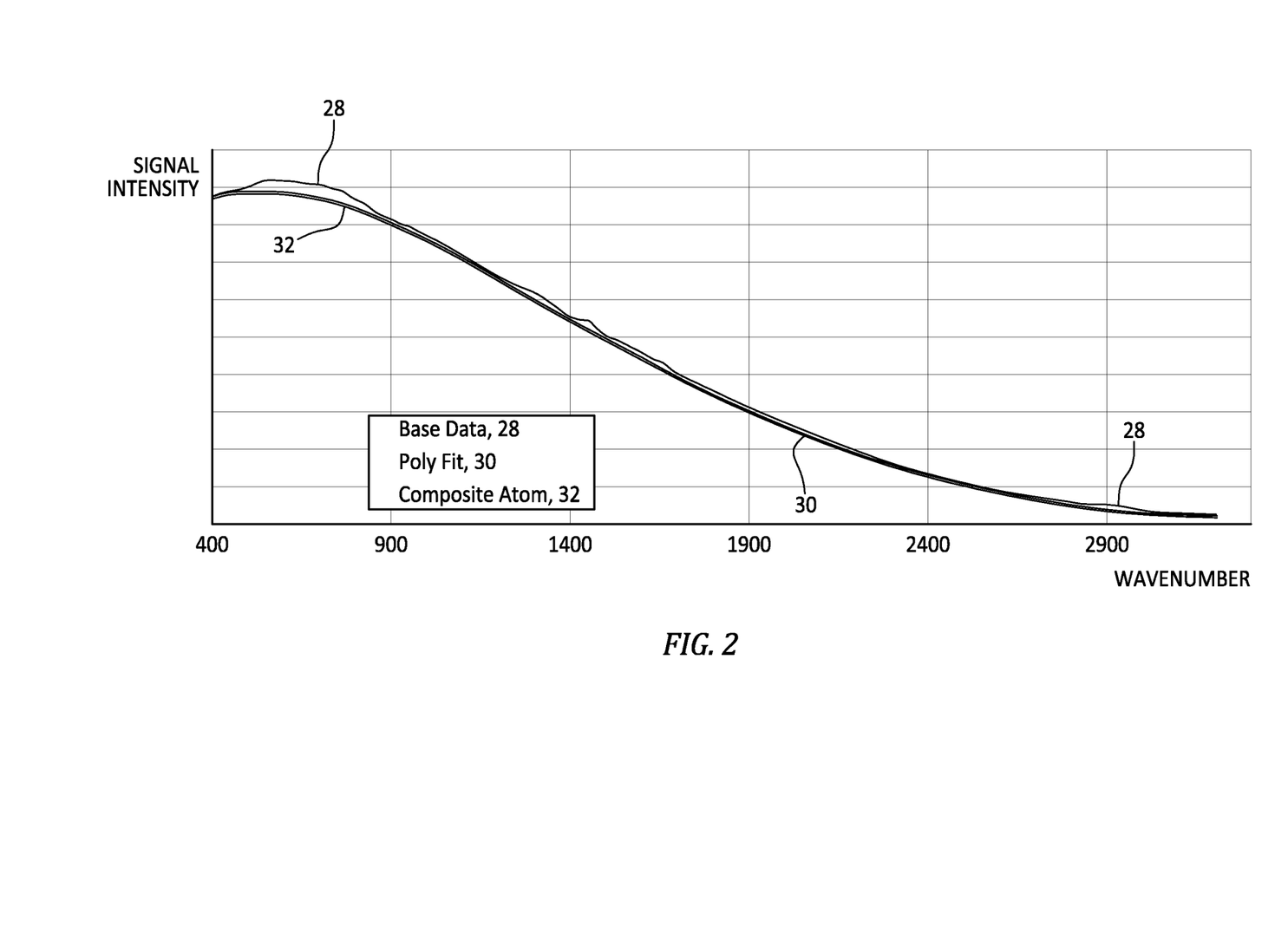
FIG. 2 is a graph of signal intensity (Y-axis) versus wavenumber (X-axis) illustrating observed spectrum produced from the interrogation of a tissue sample (base data), a curve produced using a polymeric fitting technique (Poly fit), and a reconstructed fluorescence spectrum (e.g., a composite atom).

FIG. 2 is a graph of signal intensity (Y-axis) versus wavenumber (X-axis) illustrating an observed spectrum 28 curve produced from the interrogation of a tissue sample (i.e., base data), a curve 30 produced using a polynomial fitting technique (Poly fit), and a composite atom curve 32 produced using the present disclosure techniques described above. Differences between the Poly fit curve 30 and the composite atom curve 32 stem from the fact that the Poly fit curve 30 inherently must conform to the polynomial equation whereas the composite atom 32 curve naturally conforms to the various known empirical fluorescence and absorption spectral datasets.

Figure 3:
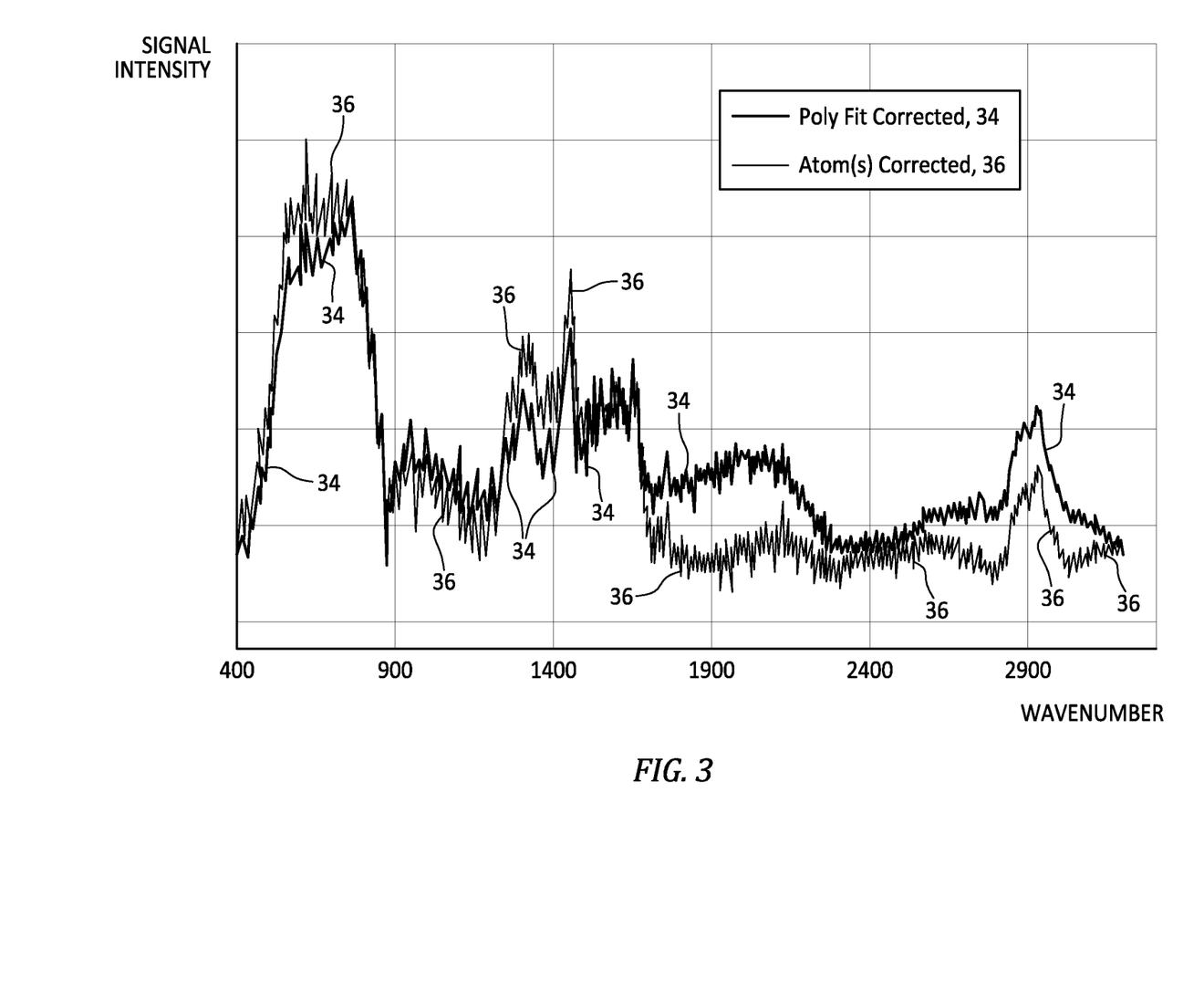
FIG. 3 is a graph of signal intensity (Y-axis) versus wavenumber (X-axis) illustrating a first curve of an observed spectrum corrected to remove the fluorescence signal using a Poly fit technique, and a second curve of an observed spectrum corrected to remove the fluorescent response using a composite atom.

FIG. 3 illustrates Raman spectra in the form of plots of Raman scattering intensity (Y-axis) versus wavenumber (X-axis), after removing the background fluorescence component from the observed spectrum using aforementioned two approaches. A first curve 34 is "corrected" to remove the background fluorescent component using a Poly fit technique, and a second curve 36 is "corrected" to remove the background fluorescence component using empirically determined fluorescent spectral profiles pursuant to the present disclosure (e.g., in the form of a composite atom). Analysis indicates that the reconstructed fluorescence spectrum based on empirically determined fluorescent spectral profiles (e.g., in the form of a composite atom) more accurately reflects the background fluorescence component of the observed spectrum, particularly in the Raman "silent region" defined as wavenumbers within the range of about 1800 $cm^1$ to about 2800 $cm^1$. The Raman signals of endogenous biospecies within the tissue matrix are typically negligible in this spectral region, thereby facilitating identification of Raman spectra. U.S. Patent Application Nos. PCT/US2020/016196 (published as WO 2020/160462) and PCT/2021/016090, both of which are hereby incorporated by reference in their respective entirety, disclose apparatus and methods for examining tissue samples in the Raman silent region.

FIG. 4A is a graph of signal intensity (Y-axis) versus wavenumber (X-axis) illustrating a fluorescence atom produced using the present disclosure. As described above, the fluorescence atom is representative of at least some of the background fluorescence component of the observed spectrum. FIG. 4B is a graph of signal intensity (Y-axis) versus wavenumber (X-axis) illustrating an absorption atom produced using the present disclosure. As described above, in some instances material (endogenous or otherwise) within the tissue sample being interrogated will absorb background fluorescence emitted as a result of the Raman spectroscopic interrogation. The absorption atom accounts for that material(s). FIG. 4C is a graph of signal intensity (Y-axis) versus wavenumber (X-axis) illustrating a composite atom produced using the fluorescence atom and the absorption atom.

As indicated above, the present disclosure is described above primarily in the context of a system 20 and method for examining a biological tissue sample; e.g., a breast tissue sample. Embodiments of the present disclosure are not, however, limited to examining biological tissue samples. The present disclosure system 20 and methods described above may be used to non-invasively examine a variety of materials (e.g., pharmaceutical products, chemical products, food products, etc.) In these applications, the empirical database of stored fluorescent spectral profiles may represent constituents normally present within the material being examined and may include fluorescent spectral profiles associated with contaminants that may be present within the material. In a similar manner to that described above, in these instances the reconstructed fluorescent spectrum would be produced to permit removal (e.g., separation) of the background fluorescence to facilitate analysis of the Raman spectroscopic analysis of the material.

While the principles of the disclosure have been described above in connection with specific apparatuses and methods, it is to be clearly understood that this description is made only by way of example and not as limitation on the scope of the disclosure. Specific details are given in the above description to provide a thorough understanding of the embodiments. However, it is understood that the embodiments may be practiced without these specific details.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements unless the context clearly indicates otherwise. As used herein, "comprises" means "includes." Thus, "comprising A or B," means "including A or B, or A and B," without excluding additional elements.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. Any reference to attached, fixed, connected or the like may include permanent, removable, temporary, partial, full and/or any other possible attachment option.

No element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Additionally, even though some features, concepts, or aspects of the disclosures may be described herein as being a preferred arrangement or method, such description is not intended to suggest that such feature is required or necessary unless expressly so stated. Still further, exemplary, or representative values and ranges may be included to assist in understanding the present application, however, such values and ranges are not to be construed in a limiting sense and are intended to be critical values or ranges only if so expressly stated.

REFERENCES

1. Gebrekidan, M. T. et al., "A Shifted-Excitation Raman Difference Spectroscopy (SERDS) Evaluation Strategy for the Efficient Isolation of Raman Spectra from Extreme Fluorescence Interference", J Raman Spectrosc., 2016, 47, 198-209.
2. Matousek, P. et al., "Fluorescence Suppression in Resonance Raman Spectroscopy Using a High-performance Picosecond Kerr Gate", J. Raman Spectrosc., 2001; 32: 983-988.
3. Lieber, C. A., & Mahadevan-Jansen, A. (2003), Automated Method for Subtraction of Fluorescence from Biological Raman Spectra, Applied Spectroscopy, 57(11), 1363-1367; https://doi.org/10.1366/000370203322554518
4. Zhao, J., Lui, H., McLean, D. I., & Zeng, H. (2007), Automated Autofluorescence Background Subtraction Algorithm for Biomedical Raman Spectroscopy, Applied Spectroscopy, 61(11), 1225-1232; https://doi.org/10.1366/00037020778297003
5. Zhong Li et al., Morphological weighted penalized least squares for background correction, Analyst, (2013) 138, 4483-4492
6. Beier, B. D. et al., Method for Automated Background Subtraction from Raman Spectra Containing Known Contaminants, Analyst, 2009; 134, 1198-1202.
7. Cadusch, P. J., Hlaing, M. M., Wade, S. A. McArthur, S. L. and Stoddart, P. R. (2013), Improved methods for fluorescence background subtraction from Raman spectra, J. Raman Spectrosc., 44: 1587-1595. doi:10.1002/jrs.4371
8. Kun Chen, Hongyuan Zhang, Haoyun Wei, and Yan Li, "Improved Savitzky-Golay-rnethod-based fluorescence subtraction algorithm for rapid recovery of Raman spectra," Appl. Opt. 53, 5559-5569 (2014)
9. Guo S X, Bocklitz T, Popp J. Optimization of Raman-spectrum baseline correction in biological application. Analyst. 2016; 141:2396-2404; doi: 10.1039/c6an00041j.
10. Vishal M. Patel, Rama Chellappa, in Handbook of Statistics, 2013

The invention claimed is:

1. A method for identifying a Raman spectrum component of an observed spectrum, the observed spectrum produced by interrogating a tissue sample with light at the one or more predetermined wavelengths, and the observed spectrum including a background fluorescence component representative of fluorescent emissions resulting from the light interrogation and a Raman spectrum component representative of a Raman scattering resulting from the light interrogation, the method comprising:
    creating a reconstructed fluorescence spectrum representative of the background fluorescence component of the observed spectrum using one or more empirically determined fluorescent spectral profiles; and
    identifying the Raman spectrum of the observed spectrum using the reconstructed fluorescence spectrum.

2. The method of claim 1, wherein the empirically determined fluorescent spectral profiles include at least one fluorescent spectral profile of a fluorophore present within the tissue sample.

3. The method of claim 2, wherein the fluorophore is at least one of tryptophan, collagen, elastin, beta-carotene, nicotinamide adenine dinucleotide (NADH), flavin adenine dinucleotide (FAD), or hemoglobin.

4. The method of claim 2, wherein the step of creating said reconstructed fluorescence spectrum includes creating a best fit between the reconstructed fluorescence spectrum and the background fluorescence component of the observed spectrum.

5. The method of claim 4, wherein the step of creating the best fit includes weighting respective contributions of a plurality of said fluorophore spectral profiles.

6. The method of claim 1, wherein the step of creating said reconstructed fluorescence spectrum utilizes an absorption spectral profile of a material that absorbs at least some of the background fluorescence component resulting from the light interrogation.

7. The method of claim 1, wherein the step of creating said reconstructed fluorescence spectrum includes using a machine learning technique.

8. The method of claim 7, wherein the machine learning technique includes sparse coding.

9. The method of claim 1, wherein the step of identifying the Raman spectrum component of the observed spectrum using the reconstructed fluorescence spectrum includes subtracting the reconstructed fluorescence spectrum from the observed spectrum.

10. A method for identifying a Raman spectrum from subject tissue using Raman spectroscopy, the method comprising:
    interrogating the subject tissue with light at the one or more predetermined wavelengths produced by at least one light source;
    determining an observed spectrum by sensing the subject tissue for light emitted from the subject tissue using one or more light detectors, the observed spectrum resulting from the light interrogation of the subject tissue, and the observed spectrum including a background fluorescence component and a Raman spectrum component;
    creating a reconstructed fluorescence spectrum representative of the background fluorescence component of the observed spectrum using one or more empirical fluorescent spectral profiles; and
    identifying the Raman spectrum component of the observed spectrum using the reconstructed fluorescence spectrum.

11. The method of claim 10, wherein the empirically determined fluorescent spectral profiles include at least one fluorescent spectral profile of a fluorophore present within the tissue sample.

12. The method of claim 11, wherein the at least one fluorophore spectral profile includes a plurality of fluorophore spectral profiles; and
the step of creating said reconstructed fluorescence spectrum includes weighting respective contributions of each of the plurality of said fluorophore spectral profiles to create a best fit between the reconstructed fluorescence spectrum and the background fluorescence component of the observed spectrum.

13. The method of claim 10, wherein the step of creating said reconstructed fluorescence spectrum utilizes an absorption spectral profile of a material that absorbs at least some of the background fluorescence component resulting from the light interrogation.

14. The method of claim 10, wherein the step of creating said reconstructed fluorescence spectrum includes using a machine learning technique.

15. The method of claim 10, wherein the step of identifying the Raman spectrum component of the observed spectrum using the reconstructed fluorescence spectrum includes subtracting the reconstructed fluorescence spectrum from the observed spectrum.

16. A system for identifying a Raman spectrum emitted from subject tissue, comprising:
at least one light source;
at least one light detector; and
an analyzer in communication with the at least one light source, the at least one light detector, and a non-transitory memory storing instructions, which instructions when executed cause the analyzer to:
control the light source to interrogate a tissue sample with light at one or more predetermined wavelengths;
control the light detector to sense an observed spectrum of light emitted from the subject tissue resulting from the light interrogation of the subject tissue, and to produce signals representative of the observed spectrum, the observed spectrum having a background fluorescence component representative of fluorescent emissions resulting from the light interrogation and a Raman spectrum component representative of a Raman scattering resulting from the light interrogation;
create a reconstructed fluorescence spectrum representative of the background fluorescence component of the observed spectrum using one or more empirically determined fluorescent spectral profiles; and
identify the Raman spectrum component of the observed spectrum using the reconstructed fluorescence spectrum.

17. The system of claim 16, wherein the empirically determined fluorescent spectral profiles include at least one fluorescent spectral profile of a fluorophore present within the tissue sample.

18. The system of claim 17, wherein the at least one fluorophore spectral profile includes a plurality of fluorophore spectral profiles; and
the instructions that cause the analyzer to create the reconstructed fluorescence spectrum also cause the analyzer to weight respective contributions of each of the plurality of said fluorophore spectral profiles to create a best fit between the reconstructed fluorescence spectrum and the background fluorescence component of the observed spectrum.

19. The system of claim 16, wherein the instructions that cause the analyzer to create said reconstructed fluorescence spectrum utilize an absorption spectral profile of a material that absorbs at least some of the background fluorescence component resulting from the light interrogation.

20. The system of claim 16, wherein the instructions that cause the analyzer to identify the Raman spectrum component of the observed spectrum also cause the analyzer to subtract the reconstructed fluorescence spectrum from the observed spectrum.

21. A method for identifying a Raman spectrum emitted from a material, the method comprising:
interrogating a material with light at the one or more predetermined wavelengths produced by at least one light source;
determining an observed spectrum by sensing the material for light emitted from the material using one or more light detectors, the observed spectrum resulting from the light interrogation of the material, and the observed spectrum including a background fluorescence component and a Raman spectrum component;
creating a reconstructed fluorescence spectrum representative of the background fluorescence component of the observed spectrum using one or more empirical fluorescent spectral profiles; and
identifying the Raman spectrum component of the observed spectrum using the reconstructed fluorescence spectrum.

22. The method of claim 21, wherein the empirically determined fluorescent spectral profiles include at least one fluorescent spectral profile of a fluorophore present within the material.

23. The method of claim 22, wherein the at least one fluorophore spectral profile includes a plurality of fluorophore spectral profiles; and
the step of creating said reconstructed fluorescence spectrum includes weighting respective contributions of each of the plurality of said fluorophore spectral profiles to create a best fit between the reconstructed fluorescence spectrum and the background fluorescence component of the observed spectrum.

24. The method of claim 21, wherein the step of creating said reconstructed fluorescence spectrum utilizes an absorption spectral profile of a second material that absorbs at least some of the background fluorescence component resulting from the light interrogation.

25. The method of claim 21, wherein the step of identifying the Raman spectrum component of the observed spectrum using the reconstructed fluorescence spectrum includes subtracting the reconstructed fluorescence spectrum from the observed spectrum.

* * * * *